US00PP07800P

United States Patent [19]

White

[11] Patent Number: Plant 7,800

[45] Date of Patent: Feb. 18, 1992

[54] POINSETTIA PLANT NAMED MARJO ROSE

[75] Inventor: James White, Stouffville, Canada

[73] Assignee: Ball Seed Co., West Chicago, Ill.

[21] Appl. No.: 611,403

[22] Filed: Nov. 9, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A Poinsettia plant named Marjo Rose particularly described by its rose color bracts, compact and freely branching habit, eight week flowering response, ability to be finished at cool night temperatures of 55° to 58° F., good post production longevity, resistance to fading, and resistance to bruising during shipping.

1 Drawing Sheet

The present invention relates to a new and distinct cultivar of Poinsettia plant known by the cultivar name Marjo Rose and botanically known as *Euphorbia pulcherrima.* Marjo Rose is a naturally occurring sport of Marjo Red and was first observed by me in the greenhouses of my business. James White Florist, Stouffville, Ontario, Canada, in 1987. It was propagated asexually by me in 1989 and flowered for one year to confirm its phenotypic stability.

Asexual reproduction by terminal cuttings taken at West Chicago, Ill. has also established that the unique features of Marjo Rose are stabilized and are reproduced true to type in successive propagations.

The following characteristics have been repeatedly observed and are determined to be basic characteristics of Marjo Rose which in combination distinguish this Poinsettia from both its parent Marjo Red and other cultivated Poinsettias of this type known and used in the floriculture industry.

1. Marjo Rose has dark pink or rose bracts, darker than Marjo Pink or Noel Hot Pink (51B). Marjo Red has red bracts.
2. Marjo Rose is a more compact than Noel Hot Pink. Marjo Rose's leaf color and plant form are similar to Marjo White and Marjo Charm.
3. Marjo Rose is freely branching with five to seven branches upon pinching.
4. Marjo Rose is an eight week cultivar, flowering one week earlier than Noel Hot Pink (nine week response). Marjo Rose flowers at the same time as Marjo Charm and Marjo White.
5. Marjo Rose's cyathia abscise earlier than Noel Hot Pink.
6. Marjo Rose can be finished at cool night temperatures of 55° to 58° F. to maximize bract color intensity.
7. Marjo Rose has good post-production longevity and is resistant to bruising during shipping. Bract color of Marjo Rose does not fade in the interior landscape like Noel Hot Pink.

The accompanying colored photograph illustrates the overall appearance of this cultivar, showing colors as true as reasonably possible to obtain in a colored reproduction of this type.

Marjo Rose has not been observed under all possible environmental conditions. The phenotype may vary significantly with variations in environment such as temperature, light intensity and daylength.

The following is a detailed description of my new Poinsettia cultivar, Marjo Rose, based on plants produced under commercial practice in West Chicago, Ill., in a glass covered greenhouse with day temperatures of 70° to 76° F. and night temperatures of 60° to 65° F.

Color references are made to The Royal Horticultural Society Colour Chart except where general terms of ordinary dictionary significance are used.

Classification:

A. *Botanical.*—*Eurphorbia pulcherrima.*

B. *Commercial.*—Poinsettia.

Parentage: Naturally occurring sport of Marjo Red.

Propagation:

A. *Type cutting.*—*Terminal.*

B. *Time to initiate roots.*—9 days at 75° F. summer; 12 days at 70° F. winter.

C. *Rooting habit.*—Excellent; well branched.

Plant description:

A. *Form.*—Freely branching, upright.

B. *Habit of growth.*—Compact.

C. *Foliage description.*—1. Size: Length, 9 to 12 cm; width, 6 to 8 cm. 2. Shape: Ovate-elliptic, some fiddle-shaped, tips acuminate. 3. Texture: Smooth. 4. Margin: Entire to lobed (fiddle-shaped). 5. Color: Mature foliage, upper surface 147A; lower surface 147B. Young foliage, upper surface 147B; lower surface 147C.

Flowering description:

A. *Flowering habits.*—Many cyathia within inflorescences that are arranged as an umbel-like cyme. Large showy bracts.

B. *Natural flowering season.*—Eight week cultivar, flowering naturally the second week of November.

C. *Bracts.*—1. Shape: Ovate with entire, sinnuate or repand margin. 2. Size: Length, 9 to 12 cm; width, 6 to 8 cm. 3. Number: Ranges from 15 to 20 per inflorescence. 4. Color: Upper surface, mature, 54A. Lower surface, mature, 54B.

D. *Cyathia.*—1. General description: Initially three main flowering stems with subsequent lateral cyathia development. 2. Borne: Upright as an umbel-like cyme. 3. Quantity: Average quantity; may abscise prematurely. 4. Color: 5D.

Reproductive organs: Typical for *Euphorbia pulcherrima* cultivars, not significant.

Disease resistance: No fungal or bacterial problems observed to date.

I claim:

1. A new and distinct cultivar of Poinsettia plant named Marjo Rose, as illustrated and described.

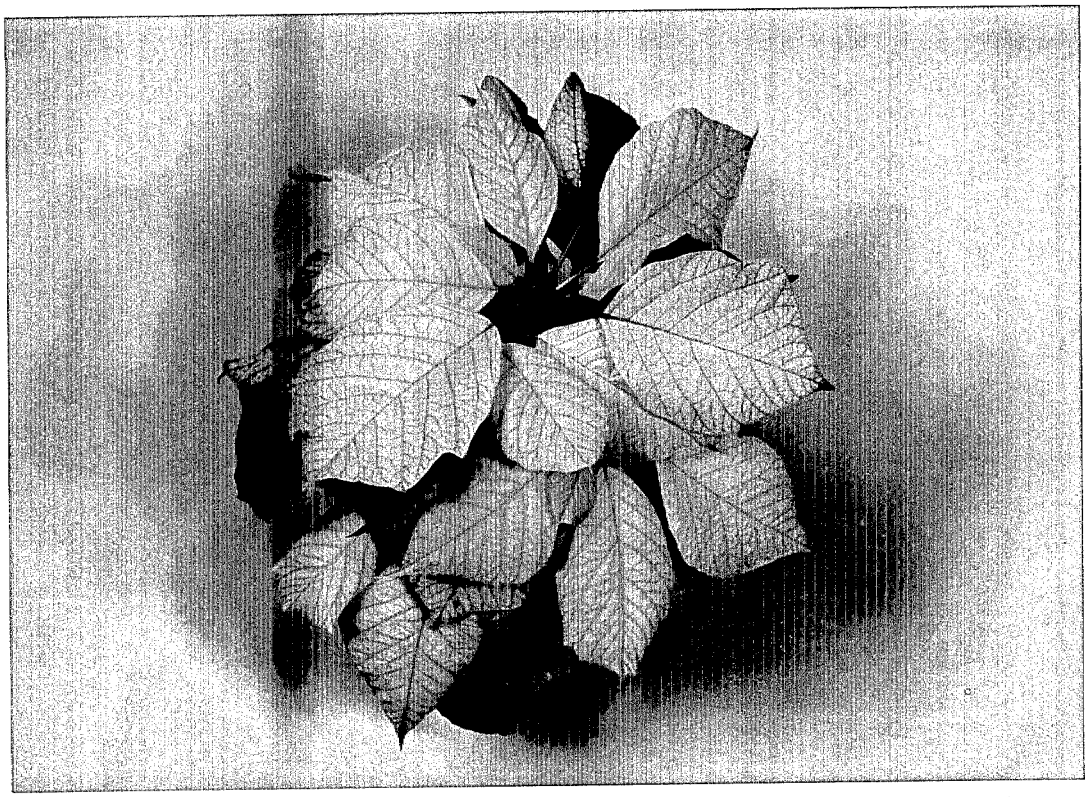

* * * * *